United States Patent [19]

Gorke et al.

[11] 4,269,626

[45] May 26, 1981

[54] AQUEOUS ACID/AMINO 1,3-BUTADIENE POLYMER REACTION PRODUCT AGENT FOR TREATING WOOD AND WOODEN MATERIALS

[75] Inventors: Klaus Gorke, Haltern-Lavesum; Wilfried Bartz, Marl, both of Fed. Rep. of Germany

[73] Assignee: Chemische Werke Heuls, A.G., Marl, Fed. Rep. of Germany

[21] Appl. No.: 73,396

[22] Filed: Sep. 7, 1979

[30] Foreign Application Priority Data

Sep. 7, 1978 [DE] Fed. Rep. of Germany ....... 2838930

[51] Int. Cl.³ ........................ C08D 5/14; C08D 5/18
[52] U.S. Cl. ........................ 106/18.32; 260/29.2 EP; 260/29.2 N; 260/29.7 H; 260/29.7 AT; 525/334; 525/337; 525/340; 525/344; 525/355; 525/379; 525/382; 528/271; 528/335; 528/363; 528/392; 564/509
[58] Field of Search ............. 106/18.32; 528/392, 528/363, 271, 335; 260/29.7 H, 29.7 AT, 29.2 N, 583 H, 583 P; 525/334, 337, 340, 355, 379, 382, 344

[56] References Cited

U.S. PATENT DOCUMENTS 3,730,951  5/1973  Braude ........................... 528/392

*Primary Examiner*—Harold D. Anderson
*Attorney, Agent, or Firm*—Millen & White

[57] ABSTRACT

An aqueous agent for treating wood and wooden materials, optionally containing customary additives, such as water-soluble wood protecting agents effective as insecticides and/or fungicides, comprises an organic binder drying by oxidation, said organic binder consisting essentially of the reaction product of an acid and a 1,3-butadiene substrate polymer modified to carry amino groups, wherein (1) the amino group carrying 1,3-butadiene polymer has a double bond content corresponding to an iodine number of at least 200 g iodine/100 g, of which a double bond content of at least 100, measured as iodine number, is derived from cis-1,4-structural elements of the 1,3-butadiene substrate polymer per se;

(2) the amino group content of the amino group carrying 1,3-butadiene polymer is at least 50 mg-atoms of nitrogen/100 g of polymer; and (3) the 1,3-butadiene substrate polymer per se has at least 70 molar percent butadiene units and a molecular weight ($\overline{M}n$) of 500–6,000.

4 Claims, No Drawings

AQUEOUS ACID/AMINO 1,3-BUTADIENE POLYMER REACTION PRODUCT AGENT FOR TREATING WOOD AND WOODEN MATERIALS

BACKGROUND OF THE INVENTION

The present invention relates to aqueous agents for treating wood and wooden materials.

Wood and wooden materials are widely popular construction materials. Due to their chemical composition and their structure, however, they possess certain naturally inherent disadvantages. For example, they are constantly exposed to the danger of attack by fungi, bacteria and insects. Additionally, large variations in their moisture content can occur having a negative effect on dimensional stability and, in the worst case, leading to fissures. Finally, their high flammability causes considerable problems from the safety technology point of view.

To more or less eliminate the above-mentioned disadvantages, it has been customary for quite some time to treat wood and wooden materials with a great variety of agents by any of a large number of methods before or after the wood has been worked on machines. Nowadays, it is even necessary in many fields of use for such treatments to meet regulating standards. In this connection, it is desirable to satisfy such requirements by simple, economical and environmentally harmless measures and to achieve an effect lasting for a maximally long period of time to avoid expensive aftertreatment processes. Particularly in the case of wood and wooden materials which are exposed to outside weathering and/or high moisture conditions, these objectives could not be completely realized heretofore.

The preferred, current methods for treating wood for preservation may be represented as follows:

(1) The introduction of wood preservatives, resistant to washing out and diffusion, from an aqueous solution. A good, durable impregnation of the marginal zones is normally achieved by this method, especially in a dipping process. However, the inner zones of thicker pieces of material are not successfully impregnated. Additionally, this method is incapable of preventing the occurrence of cracks caused by great moisture fluctuations; in part, unprotected zones are formed, since all active agents are fixed in the marginal zone. Attempts have been made to overcome this deficiency by simultaneously using, in certain cases, in addition to the fixable preservatives, water-soluble active agents which are not fixable and thus remain capable of diffusion. However, this protection is also not permanent when cracks occur, since the unfixed active agents are then washed out by the effects of the weather. If longer lasting protection is desired, an additional surface treatment by application of an organic coating is required.

(2) The introduction of wood preservatives, which are water-insoluble or sparingly soluble in water, from organic solvents. The capability of these active agents to diffuse in wood having a sufficiently low moisture content is satisfactory; however, this method is likewise incapable of preventing cracks. Additionally, several of these often highly toxic preservatives have a marked vapor pressure. For these reasons, an additional treatment with an organic coating agent is also recommended here. Furthermore, a quite substantial disadvantage of this method is the use of organic, flammable and, in part, physically harmful solvents.

The above mentioned post treatment of the impregnated components with an organic coating normally takes place in a separate operating step. However, efforts have already been made to obviate this additional treatment step by the use of binder-containing wood preservatives. In these agents, synthetic resin dispersions were preferably used as the binders for the ingredients applied from aqueous solution, and alkyd resins and related systems were preferred for those applied from organic solvents.

One disadvantage in both cases is the low penetrating power of the organic binders. Additionally, for the binder-containing wood preservative systems, based on organic solvents, the binder content must be kept at a very low value; otherwise, the penetration of the preservative active agents is impeded. This makes it necessary to repeat the treatment until sufficient film thicknesses have been achieved. As a result, this mode of operation does not offer any economical advantages over a subsequent coating step. Moreover, the penetrating power of aqueous synthetic resin dispersions is even lower than that of the organic solvent-containing systems. Accordingly, the wood preservation effect attainable in all cases is moderate at best.

Consequently, the active ingredients added to aqueous impregnating agents serve more for preserving the coating agent prior to impregnation than for protecting the substrate to be treated. There is almost no regulation of moisture absorption and emission by the treated wood.

The known water-dilutable alkyd resin emulsions alkyd-resin-containing synthetic resin dispersions and water-dilutable alkyd resins are also subject to essentially the same disadvantageous features discussed for the water-dilutable glazings based on synthetic resin dispersions.

Prior to treating coniferous woods with the latter agents, priming with an officially admitted, wood-preserving primer is recommended or even required.

SUMMARY OF THE INVENTION

It is an object of the present invention to provide an aqueous treating agent for wood and wooden materials which is free of the foregoing disadvantages and which contains an organic binder which dries by oxidation and which has been made soluble by treatment with acids; the agent having a high penetrating power and ensuring a permanent wood protection, optionally in conjunction with water-soluble additives having, e.g., insecticidal and/or fungicidal activity.

Upon further study of the specification and appended claims, further objects and advantages of this invention will become apparent to those skilled in the art.

These objects have been attained by providing a wood and wooden material treating agent containing as an organic binder a low-molecular weight 1,3-butadiene polymer having amino groups, the binder having:

(1) a double bond content corresponding to an iodine number of at least 200 g iodine/100 g, of which a double bond content of at least 100, also measured as the iodine number (g iodine/100 g) is due to cis-1,4-structural elements of the 1,3-butadiene polymer;

(2) an amino group content of at least 50 mg-atoms of nitrogen/100 g of binder; and (3) a substrate polymer, for the amino-group-carrying 1,3-butadiene polymer having at least 70 molar percent butadiene units and a number average molecular weight of 500–6,000.

DETAILED DISCUSSION

The term "wooden materials" comprises, within the scope of this invention, those materials which extensively exhibit the typical spectrum of characteristics inherent in wood. Among these are, for example, laminboard and plywood.

Homo- and copolymers of 1,3-butadiene may be employed as the basic polymers for preparing the organic binders of the treating agents of this invention. Suitable comonomers are primarily other conjugated diolefins, such as 1,3-pentadiene, 1,3-dienes of the homologous series and isoprene. Such comonomers may be employed in amounts of 0–30 molar %, preferably 0–10 molar %. Furthermore, suitable as comonomers in lower amounts, e.g., 0–20 molar %, preferably 0–10 molar %, are monoolefins such as ethylene, propylene, etc. or aromatic vinyl compounds, such as styrene, for example.

The butadiene polymers must contain at least 70 molar percent of butadiene units; preferably, they contain at least 90 molar percent of butadiene units. Especially suitable as the treating agents of this invention are binders based on homopolybutadiene as the substrate polymer. The preferred number average molecular weight ($\overline{M}n$) for this substrate polymer is 500–3,000 as determined by vapor pressure osmometry. Such polymers can be produced in accordance with conventional methods of the state of the art, for example, according to the processes of German Pat. Nos. 1,186,631; 1,212,302; 1,241,119; 1,251,537; and 1,292,853; and DOS (German Unexamined Laid-Open Application) 2,361,782, the disclosures of which are incorporated by reference herein.

The introduction of amino groups into these low-molecular weight 1,3-butadiene polymers can be conducted according to various conventional methods.

A preferred procedure (I) produces, via the chemical addition of $\alpha,\beta$-unsaturated dicarboxylic acids or the anhydrides thereof and subsequent reaction of the addition products with primary-tertiary diamines, aminodicarboxylic acid imide adducts.

An especially preferred method (II) proceeds by epoxidation of the 1,3-butadiene polymers and subsequent reaction of the epoxides with primary and/or secondary aliphatic amines.

Further details regarding the introduction of amino groups into the low-molecular weight 1,3-butadiene polymers according to methods (I) and (II) can be obtained, for example, from DOS Nos. 2,616,591; 2,728,470; 2,734,413; and 2,732,736.2, the disclosures of which are incorporated by reference herein.

As starting materials for both methods (I) and (II), the 1,3-butadiene polymers can be employed directly as they are obtained during conventional manufacture; or they can first be modified using known methods, such as, for example, partial hydrogenation, isomerization and/or cyclization.

An essential feature for attaining the objective of this invention is the requirement that the amino-group-carrying, low-molecular weight 1,3-butadiene polymers used as the binders for the treating agent of this invention possess a double bond content corresponding to an iodine number of at least 200, preferably at least 250 g iodine/100 g. A certain proportion of this total double bond content corresponding to a Wijs iodine number of at least 100, preferably at least 150 (g iodine/100 g), must be derived from cis-1,4-structural elements of the 1,3-butadiene polymer.

To impart to the amino-group-carrying, low-molecular weight 1,3-butadiene polymers a sufficient water solubility or water dispersibility after a subsequent reaction with acids, an amino group content of at least 50 mg-atoms of nitrogen/100 g of binder is required. A content of 100–400 is preferred; quite especially preferred is a content of 120–300 mg-atoms of nitrogen/100 g of binder. With increasing amino group content, the solubility of the acid-neutralized binders and the stability of the aqueous binder solution are increased. Solubility and stability can also be improved by the introduction of amino groups carrying hydropholic substituents.

Among the large number of binders suitable for inclusion in the treating agent of this invention, the following are preferred:

Binders prepared according to method (I) obtained by the reaction of (a) an adduct of 18–25% by weight of maleic anhydride and 82–75% by weight of a polybutadiene having a molecular weight ($\overline{M}n$) of 800–2,000, an iodine number of $\geq 350$ (g iodine/100 g) and a cis-1,4-content of $\geq 70\%$ of the double bonds present, with (b) a 1,3-diaminopropane of the formula

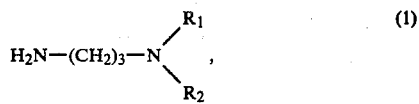

wherein $R_1$ and $R_2$ independently are each alkyl of up to 4 carbon atoms or together represent —$(CH_2)_5$— or —$(CH_2)_2$—O—$(CH_2)_2$—, i.e., are components of a ring.

A portion of the 1,3-diaminopropane can be replaced by an amine of the formula $R_3$—$NH_2$ wherein $R_3$ is H or alkyl of up to 4 carbon atoms, insofar as it is ensured that the binder contains a quantity of amino groups corresponding to at least 120 mg-atoms of nitrogen/100 g binder.

The binders produced according to method (II) are especially preferred, which are obtained by the reaction of (a) epoxidized polybutadiene with an epoxy content, determined according to DIN [German Industrial Standard]16 945, of 5–8% by weight of oxygen, prepared from a polybutadiene having a molecular weight ($\overline{M}n$) of 1,000–2,500, an iodine number of $\geq 350$ g iodine/100 g, and a cis-1,4-content of $\geq 70\%$ of the double bonds present, with (b) one or more amines of the formulae (2)

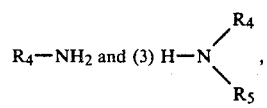

wherein $R_4$ and $R_5$ independently are each alkyl of up to 4 carbon atoms or hydroxyalkyl of 2–4 carbon atoms, or in Formula (3) together represent —$(CH_2)_5$— or —$(CH_2)_2$—O—$(CH_2)_2$—, i.e., are components of a ring. Especially suitable is the use or concomitant use of 1,3-diaminopropanes of Formula (1). The amino group content in the final product is to be at least 120 mg-atoms of nitrogen/100 g of binder.

The thus-obtained addition products are converted into their water-soluble or water-dispersible salt forms by neutralization or partial neutralization with acidic compounds. The nature of the acid is not critical as long as it is otherwise system compatible. Suitable acidic compunds include inorganic acids, such as, for example, sulfuric acid, hydrochloric acid, boric acid and phosphoric acid, or, alone or in a mixture therewith, organic acids, such as formic acid, acetic acid, propionic acid, butyric acid, lactic acid and similar compounds.

To attain sufficient solubility or dispersing capacity of the binders in water, the amount of acid added must be adequately high. The higher the concentration of the amino groups in the addition compound used as the binder, the lower will be the degree of neutralization required to attain the desired effect. Normally, the minimum amount of acid required is 0.3–0.5 equivalent of acid/equivalent of amino group. With respect to the binder there is no critical upper limit for the acid. With increasing amount of acid, the stability of the aqueous binder solution rises, manifesting itself, for example, by an improved compatibility with respect to electrolyte additives and by an increased penetration power.

Thus, it may be advantageous in certain cases to use 5 and more equivalents of acid/equivalent of amino group. In these instances, it is then also expedient to use at least in part those acids which conventionally display a wood-preserving effect, such as, for example, boric acid and phosphoric acid. The pH values of the aqueous treating agents are 2–8, depending on the chemical nature of the binders and additives employed, as well as on the acid utilized.

The binders, once reacted with acids, can be mixed with water to an unlimited extent. However, it has been found under practical conditions that the addition of certain amounts of conventional organic solvents, prior to or after addition of the acid to the binder, facilitates the preparation of the treating agent and increases its stability. These measures are basically known to those skilled in the art. For this purpose, it is possible to use organic solvents, such as isopropanol, butanols, diacetone alcohol, alkyl "Cellosolves", and dimethyl ethers of glycols. These solvents are utilized in amounts of up to 100 parts by weight, preferably 5–50 parts by weight, and especially in amounts of 10–40 parts by weight, per 100 parts by weight of binder.

Since the binders utilized in the treating agents according to this invention are dried by oxidation, it is usually unnecessary to add additional resins as cross-linking agents. Of course, other binders having a cross-linking effect—in some cases with heat treatment—can be used concomitantly, such as, for example, water-soluble or water-dispersible aminoplasts or phenolic resins, insofar as they are otherwise compatible, i.e., as long as the effect desired within the scope of the objectives of this invention is not substantially impaired.

In addition, the treating agents of this invention can also contain conventional additives, such as pigments, stabilizers, driers, surfactants, viscosity regulators and, especially, those additives known as wood preservatives. These include primarily water-soluble wood preservatives having an insecticidal and/or fungicidal effect, e.g., alkali fluorides, alkali arsenates, fluosilicates, hydrogen fluorides, inorganic boron compounds (boric acid, borates) and heavy metal salts of lead, cadmium, nickel, cobalt, manganese, copper, mercury and zinc. When adding chromates, compatibility must be tested in each particular case.

The additives can be included in amounts customary under practical conditions. These amounts are also dependent on the respective material to be treated, its purpose of use, and the method of impregnation, and are readily determinable by several routine orientation tests.

The treating agents of this invention generally have a binder content of 1–30% by weight, preferably 5–15% by weight and can be used in accordance with all conventional processes (see DIN 68 800, sheet 3) of the prior art. In this connection, the protective effect attainable is, as is known to those skilled in the art, narrowly linked to the treatment method.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

A. Basic Polymers

Two different basic substrate polymers are employed for preparing the treating agents of this invention:
(a) Homopolybutadiene (iodine number according to Wijs: 445; 1,4-cis: 1,4-trans: vinyl =73:25:2; molecular weight: 1,700; viscosity [20° C.] ~800 mPa·s).
(b) Homopolybutadiene (iodine number: 435; 1,4-cis: 1,4-trans:vinyl =48:13:39; molecular weight: 1,300; viscosity [20° C.] according to Brookfield: ~940 mPa·s).

B. Preparation of 1,3-Butadiene Polymers Carrying Amino Groups —hereinafter referred to as Amino Adducts (a) According to Method I:

EXAMPLE 1

1,300 g of basic polymer (a) and 275.8 g of maleic anhydride (MA) are reacted in the presence of 1.5 ml of acetylacetone and 1.6 g of a commercially available antioxidant [DPPD [=N,N'-dipheylparaphenylenediamine] under nitrogen for one hour at 180° C. and then for 3 hours at 190° C. The MA adduct contains ≦0.1% by weight of free MA and has an acid number of 177 mg KOH/g (titrated in pyridine/water). In an agitator flask with reflux condenser, 600 g of this MA adduct is combined under agitation and under nitrogen with 107.9 g of N,N-dimethyl-1,3-propylenediamine at 120°–130° C. within 5 hours, this latter compound being added dropwise. After another 2 hours at this temperature, the temperature is raised to 150° C. After 5 hours at 150° C., the reaction mixture is heated to 180° C., and while passing nitrogen through the melt the volatile components are driven off. The thus-obtained amino adduct 1 has an acid number of <3 mg KOH/g and an amino group content corresponding to 130 mg-atoms of nitrogen/100 g. After the addition of 11 g of 50% by weight acetic acid to 100 g of a 90% by weight solution of the amino adduct 1 in isopropanol, the mixture can be diluted with water to an unlimited extent.

EXAMPLE 2

Under the reaction conditions of Example 1, 820 g of basic polymer (a) is reacted with 180 g of MA (1 ml of acetylacetone; 1 g of DPPD). The thus-obtained MA adduct is dissolved in 500 g of isopropanol and, after adding 113 g of N,N-dimethyl-1,3-propylene-diamine, is reacted in an autoclave for 5 hours at 180° C. After cooling to room temperature, 50 ml of liquid $NH_3$ is forced into the autoclave, and the mixture is heated once again for 5 hours to 180° C. The discharge from the autoclave is concentrated at 2 mbar and 100° C. until the weight remains constant. The amino adduct 2 has an acid number of 3 mg KOH/g, a total nitrogen content of 3.8% by weight, and an amino group content corresponding to 98 mg-atoms of nitrogen/100 g. An 80% by weight solution of the amino adduct 2 in butyl glycol can be diluted with water to an unlimited extent after the addition of 9 g of 50% by weight acetic acid per 100 g of solution.

(b) According to Method II:

Epoxidation 20.0 kg of homopolybutadiene (a) is dissolved in 60.0 kg of $HCCl_3$ and heated to boiling. A mixture of 5.0 kg of 60% $H_2O_2$ and 0.9 kg of formic acid is added dropwise within 90 minutes; then the reaction mixture is maintained at the boiling point for another 5 hours. After cooling, the organic phase is washed with water at 20° C. until it is free of acid and $H_2O_2$. The principal amount of the water is removed in a separating funnel; the remainder is eliminated during the distillation of the chloroform. After withdrawing the chloroform under vacuum, 20.2 kg of a clear, colorless epoxidized butadiene polymer is obtained having a viscosity (20° C.) of 2.9 Pa.s. Yield: 94%.

The thus-obtained epoxidized 1,3-butadiene polymer is denoted by I in the Table below. The products denoted by II to IV are prepared analogously to the above directions. Basic polymer (b) was utilized for the preparation of III.

For preparing the amino adducts 3-7 below, these epoxidized 1,3-butadiene polymers are utilized and have the following properties:

| Epoxidized 1,3-Butadiene Polymer | Epoxy Oxygen (% Oxygen, Acc. to DIN 16 945) | Iodine* Number |
|---|---|---|
| I | 4.78 | 314 |
| II | 7.23 | 258 |
| III | 4.60 | 302 |
| IV | 5.59 | 296 |

*Recalculated measured value; double bonds are determined by IR spectroscopy.

EXAMPLE 3

300 g of epoxidized 1,3-butadiene polymer I is mixed under nitrogen with 46.5 g of diethanolamine and reacted under agitation at 190° C. After 6 hours, the amine has been reacted practically quantitatively. The product contains 129 mg-atoms of nitrogen/100 g of adduct 3 and 2.05% by weight of residual epoxy oxygen.

EXAMPLE 4

300 g of epoxidized 1,3-butadiene polymer II is reacted quantitatively according to Example 3 with 70.7 g of diethanolamine in the presence of 0.2% by weight of Cu naphthenate at 190° C. After 4.5 hours, a product is obtained with 183 mg-atoms of nitrogen/100 g of adduct 4 and 2.92% by weight of residual epoxy oxygen.

EXAMPLE 5

800 g of epoxidized 1,3-butadiene polymer III is quantitatively reacted analogously to Example 3 with 118 g of diethanolamine at 190° C. After 5 hours, a product is obtained with 122 mg-atoms of nitrogen/100 g of adduct 5 and 2.0% by weight of residual epoxy oxygen.

The amino adducts 3-5 are dissolved to an extent of 80% by weight in isopropanol. After the addition of 70 equivalent percent of acetic acid, based on the amino group content, all solutions can be diluted with water to an unlimited degree.

EXAMPLE 6

1,200 g of epoxidized 1,3-butadiene polymer IV and 158 g of monoethanolamine are reacted for 6 hours at 160° C. and then for 3 hours at 190° C. under nitrogen. An adduct 6 is obtained having an amino group content corresponding to 186 mg-atoms of nitrogen/100 g and with 1.64% by weight of residual epoxy oxygen. The amino adduct 6 is diluted with isopropanol to a solids content of 70% by weight, combined with 200 equivalent percent of acetic acid (based on the amino group content), and then diluted with water to a solids content of 10% by weight. The pH of the solution is 4.0.

It is possible, for example to introduce into this solution 4.5% by weight of boric acid ($H_3BO_3$) or 1.5% by weight of potassium bifluoride, based on the aqueous treating agent, without coagulation of the binder. Compatibility with respect to copper sulfate ($CuSO_4.5H_2O$) is below 1% by weight.

EXAMPLE 7

1,268.5 g of epoxidized 1,3-butadiene polymer IV and 163.4 g of N,N-dimethyl-1,3-propylenediamine are gradually heated under nitrogen to 180° C. After 5 hours at 180° C., 166.1 g of diethanolamine is added thereto, and the mixture is heated to 200° C. After 8 hours at 200° C., nitrogen is passed through the melt for another 2 hours at 200° C. to remove volatile components. The thus-obtained amino adduct 7 has an amino group content corresponding to 298 mg-atoms of nitrogen/100 g and 0.2% by weight of residual epoxy oxygen.

Analogously to Example 6, a 10% by weight solution is prepared from the amino adduct 7. The pH is 4.1.

It is possible, for example, to stir into this solution 5% by weight of $H_3BO_3$, 5% by weight of $CuSO_4.5H_2O$, or 10% by weight of $KHF_2$ without coagulation of the binder.

C. Impregnation Tests

The 10% by weight solution of the amino adduct 7 prepared in Example 7 will be denoted as treating agent 1 in the following description. By dissolving 4 parts by weight of $H_3BO_3$ and 5 parts by weight of $CuSO_4.5H_2O$ in 91 parts by weight of treating agent 1, a water-soluble treating agent 2 containing wood preservatives is produced. For comparison purposes, treatment agent A is prepared by dissolving 4 parts by weight of $H_3BO_3$ and 5 parts by weight of $CuSO_4.5H_2O$ in 91 parts by weight of water. At room temperature, small pinewood blocks (about $19 \times 15 \times 65$ mm) are placed in these treating agents; these blocks contain 10% by weight of moisture (determined as weight loss by 3 hours of drying at 130° C.).

After 1, 2 and 4 hours, blocks are taken from the various treatment baths. The superficial moisture is removed from the blocks with filter paper. Thereafter, the weight gain of the blocks is determined. The thus-obtained values (%) are entered in column 3 of the table below. Thereafter, the impregnated blocks are dried for 3 hours at 130° C. and then weighed once again. The weight increase in percent gained by the blocks, in each case based on the dried condition, is entered in column 4. Column 5 shows the percentage of the amount of treating agent remaining in the wood after drying.

That is, these values are:
Column 3: $(I-G/G) \cdot 100$ (absorption in the wet state)
Column 4: $(W-T/T) \cdot 100$ (absorption in the dry state)
Column 5: $(W-T)/(I-G) \cdot 100$ (relative absorption in the dry state)

wherein:
G = weight of the wood, untreated, without drying
T = weight of the wood, untreated, dried
I = weight of the wood, impregnated, without drying
W = weight of the wood, impregnated, dried.

As can be seen from the table, the relative absorption in the dry state (column 5) for the treating agent 1 corresponds very well to its binder content. On the other hand, the penetrating power of the treating agents of this invention is nowise reduced by the presence of the binder; rather, it is increased. The same holds true for the penetrating power of the inorganic wood preservatives added to the treating agents of the present invention.

TABLE
IMPREGNATING TESTS

| Treating Agent | Impregnang Period (h) | Absorption in the Wet State (%) | Absorption in the Dry State (%) | Relative Absorption in the Dry State (%) |
|---|---|---|---|---|
|   | 1 | 35.1 | 4.1 | 10.4 |
| 1 | 2 | 35.8 | 3.7 | 9.3 |
|   | 4 | 43.1 | 4.5 | 9.5 |
|   | 1 | 35.3 | 5.5 | 14.1 |
| 2 | 2 | 41.9 | 6.4 | 13.9 |
|   | 4 | 62.4 | 10.1 | 14.6 |
|   | 1 | 32.3 | 1.2 | 3.5 |
| A | 2 | 34.7 | 1.7 | 4.4 |
|   | 4 | 42.1 | 1.7 | 3.7 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An aqueous agent for treating wood and wooden materials, comprising an organic binder dryable by oxidation and consisting essentially of the reaction product of an acid and an amino group carrying 1,3-butadiene substrate polymer, wherein (1) the amino group carrying 1,3-butadiene polymer has a double bond content corresponding to an iodine number of at least 200 g iodine/100 g, of which a double bond content of at least 100, measured as iodine number, is derived from cis-1,4-structural elements of the 1,3-butadiene substrate polymer per se;

(2) the amino group content of the amino group carrying 1,3-butadiene polymer is at least 50 mg-atoms of nitrogen/100 g of polymer; and (3) the 1,3-butadiene substrate polymer per se has at least 70 molar percent butadiene units and a number average molecular weight of 500–6,000, said reaction product being a water soluble or water dispersible salt.

2. The aqueous agent of claim 1 further comprising a wood preserving ingredient.

3. The aqueous agent of claim 2, wherein the wood preserving ingredient is a water-soluble insecticide or fungicide.

4. The aqueous agent of claim 1, wherein the 1,3-butadiene substrate polymer which carries amino groups is prepared by reacting (a) an adduct of 18–25% by weight of maleic anhydride and 82–75% by weight of a polybutadiene having a number average molecular weight of 800–2,000, an iodine number of $\geq 350$ g iodine/100 g and a cis-1,4-content of $\geq 70\%$ of the double bonds present, with (b) a 1,3-diaminopropane of the formula

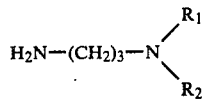

wherein $R_1$ and $R_2$ independently are each alkyl of up to 4 carbon atoms or together represent $-(CH_2)_5-$ or $-(CH_2)_2-O-(CH_2)_2-$; or (a) epoxidized polybutadiene with an epoxy content of 5–8% by weight of oxygen, prepared from a polybutadiene having a number average molecular weight of 1,000–2,500, an iodine number of $\geq 350$ g iodine/100 g, and a cis-1,4-content of $\geq 70\%$ of the double bonds present, with (b) an amine of the formula $R_4-NH_2$ or $HNR_4R_5$ wherein $R_4$ and $R_5$ independently are each alkyl of up to 4 carbon atoms or hydroxyalkyl of 2–4 carbon atoms, or together represent $-(CH_2)_5-$ or $-(CH_2)_2-O-(CH_2)_2-$.

* * * * *